United States Patent [19]

Chupp et al.

[11] Patent Number: 4,469,890
[45] Date of Patent: Sep. 4, 1984

[54] PREPARATION OF ORTHO-AMINOBENZOTRIFLUORIDE

[75] Inventors: John P. Chupp, Kirkwood; Thomas E. Neumann, Creve Coeur; Michael J. Miller, Manchester, all of Mo.

[73] Assignee: Monsanto Company, St. Louis, Mo.

[21] Appl. No.: 530,152

[22] Filed: Sep. 7, 1983

[51] Int. Cl.³ .................. C07C 85/00; C07C 85/11
[52] U.S. Cl. .................................. 564/417; 564/419
[58] Field of Search ................................ 564/417

[56] References Cited
U.S. PATENT DOCUMENTS

| | | | |
|---|---|---|---|
| 2,772,313 | 11/1956 | Trager | 564/417 |
| 3,073,865 | 1/1963 | Spiegler | 564/417 |
| 3,359,315 | 12/1967 | Kosak | 564/417 |
| 3,457,310 | 7/1969 | Fischback et al. | 564/417 X |
| 3,474,144 | 10/1969 | Craig et al. | 564/417 |

Primary Examiner—Paul F. Shaver
Attorney, Agent, or Firm—Robert B. Martin; Richard H. Shear

[57] ABSTRACT

This invention relates to a process for the preparation of ortho-aminobenzotrifluoride (OABT) from benzotrifluoride (BTF). The process provides an overall route employing non-isolation of intermediates which can be run smoothly and which results in the preparation of OABT in high yields with less contamination. This process includes a catalytic halogenation step in which BTF is converted to meta-halo BTF and other mono and di-halo isomers of BTF followed by nitration in the same reaction vessel under conditions which do not favor nitration of the di-halo isomers of BTF to produce a mixture which predominates in 5-halo-2-nitro BTF. In the final step the 5-halo-2-nitro BTF present is reduced and hydrodehalogenated with $H_2$ in the presence of a catalyst to form OABT. Recyclable BTF is also obtained from the final reaction.

4 Claims, No Drawings

PREPARATION OF ORTHO-AMINOBENZOTRIFLUORIDE

BACKGROUND OF THE INVENTION

1. Field of the Invention

This invention relates to a process for the preparation of ortho-aminobenzotrifluoride from benzotrifluoride.

2. Description of the Prior Art

Ortho-aminobenzotrifluoride (OABT) is a valuable intermediate product useful in the manufacture of important products in various fields such as dyestuffs, herbicides and the like. A number of prior art methods have been disclosed for the preparation of OABT. Most industrial production of OABT has resulted from recovering small quantities of by-product OABT in the production of meta-aminobenzotrifluoride. Nitration of benzotrifluoride produces a mixture of nitro trifluoromethylbenzenes, containing only about 8 to 10% of the 2-nitrotrifluoromethylbenzene isomer. Upon reduction of the mixture OABT is obtained in yields of 8 to 10%.

Various other complicated pathways for the more specific production of OABT have been described in the literature. See Tetrahedron 8, p. 67 (1960) which illustrates a lengthy series of steps beginning with 3-acetamidotrifluoromethylbenzene. Another described procedure involves hydrolysis and Hoffmann rearrangement of 2-trifluoromethylbenzonitrile after side chain chlorination and subsequent fluorination of 2-methylbenzonitrile with SbF$_3$. See Z. Obsch. Chim. 23, 988 (1953). OABT production employing o-toluidine as the starting point has also been described. See German Patent 627,371 and U.K. Patent 459,890. In this process the amino group in o-toluidine is protected by acylation with phthalic acid followed by chlorination and subsequent fluorination of the CH$_3$ substituent. OABT is obtained upon hydrolysis of the protective acyl group.

Each of the individual steps of the overall process of the present invention (i.e., halogenation, nitration and reduction) have been described in the literature. See, for example, Holt et al U.S. Pat. No. 2,174,513; Robota et al U.S. Pat. No. 3,234,292; Ligett U.S. Pat. No. 2,654,789; Heyna Ger. 637,318; Kageyama et al, Kogyo Kagaku Zasshi, 65, pp. 1203–07 (1962); Jones, J.Am. Chem. Soc., 69, pp. 2346–50 (1947). Kosak, Annals of New York Academy of Science, 172, pp. 175–85 (1970); German Offen. No. 3017542; EPO Application No. 0 038 465; EPO Application No. 0 054 464. The processes of the foregoing references have not led to a smooth and economical overall process for producing OABT in high yields with low off-isomer contamination.

Accordingly, it is an object of the present invention to provide a process for the smooth and efficient conversion of benzotrifluoride to ortho-aminobenzotrifluoride which lends itself to commercial production methods.

It is a further object of the present invention to provide a multi-step process for the conversion of benzotrifluoride to ortho-aminobenzotrifluoride which achieves high OABT yields with lower contamination by the meta-aminobenzotrifluoride (MABT) isomer.

SUMMARY OF THE INVENTION

In accordance with the foregoing objectives and others which will be readily apparent to those skilled in the art, the present invention provides a process for preparing ortho-aminobenzotrifluoride which process comprises the steps of (a) reacting benzotrifluoride with a halogen selected from the group consisting of chlorine and bromine in the presence of a catalyst selected from the group consisting of FeCl$_3$, Fe/FeCl$_3$, and SbCl$_5$ to produce a crude halogenation reaction mixture containing meta-halobenzotrifluoride and other mono and dihalo substituted benzotrifluorides; (b) reacting said crude halogenation reaction mixture with nitric acid in the presence of sulfuric acid to from a crude organic nitration reaction mixture said reaction being carried out at a temperature at which the monohalobenzotrifluoride isomers are preferentially nitrated but the dihalo isomers do not undergo appreciable nitration; (c) reacting said crude organic nitration reaction mixture with hydrogen in the presence of a hydrogenation catalyst and a hydrogen halide scavenger to produce a mixture of ortho-aminobenzotrifluoride, other amino-substituted isomers of benzotrifluoride and unsubstituted benzotrifluoride; and (d) separately recovering ortho-aminobenzotrifluoride product and recyclable benzotrifluoride for use in step (a).

The ortho-aminobenzotrifluoride produced according to the present invention has a wide variety of known uses including as starting materials in the production of herbicides and the like.

DETAILED DESCRIPTION OF THE INVENTION

The first step of the present invention involves the reaction of benzotrifluoride (BTF) with a halogenating agent to produce a mixture of mono and di-halo-substituted benzotrifluorides. This reaction can be schematically illustrated as follows:

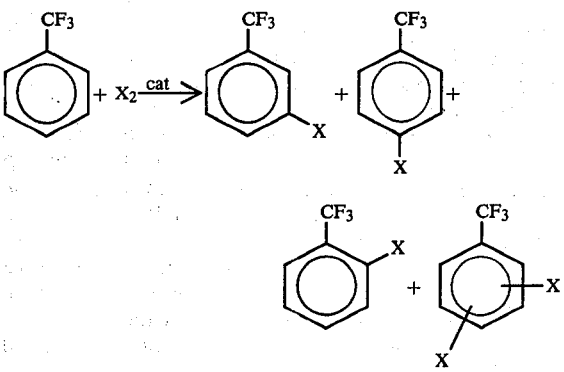

where X is a halogen selected from the group consisting of Cl or Br.

Benzotrifluoride is a commercially available material which can be prepared by a number of known routes including the chlorination and subsequent fluorination of toluene. Commercially available halogenating agents such as gaseous chlorine or liquid bromine are preferred. The halogenation reaction is effected in the presence of a suitable catalyst system such as FeCl$_3$, Fe/FeCl$_3$, or SbCl$_5$. The preferred catalyst system comprises a mixture of solid powdered iron and powdered anhydrous iron chloride (III). While in general stoichiometric amounts of halogen and BTF may be employed, it is preferred to ultilize a molar excess of the halogen reagent, e.g., from about 1.1 to about 2.0 equivalents of halogen per equivalent of BTF. Catalysts may be employed in conventional amounts and generally do not exceed about 5 to 10% by weight of the other reagents.

The reaction of BTF with halogen such as chlorine may be effected in any convenient reaction vessel adapted to permit introduction of the halogenation agents. In the preferred embodiment benzotrifluoride along with the catalyst system is charged to a stirred reactor into which gaseous chlorine is subsequently bubbled. The exit gases from the reactor may be passed through a condenser to recover entrained starting materials and product.

The halogenation reaction is mildly exothermic and heating or cooling may be employed to facilitate appropriate reaction temperature control. Preferred reaction temperatures are less than about 80° C. with from about 15° to 40° C. being most preferred. Chlorination is preferably effected at about 30° C. or less. The halogenation requires a reaction period of preferably about 8 to 10 hours. In general, the reaction is terminated when about 97% of the BTF has been consumed.

Once the reaction has gone to completion the catalyst can be optionally removed from the crude reaction product by allowing the mixture to settle and decanting the liquid product from the solid catalyst. The subsequent nitration step, however, can be employed on the crude reaction mixture without separation of the catalyst at this point. Typical yields for this first reaction step (chlorine is the halogenating agent) are as follows:
benzotrifluoride—1–4%,
3-chloro-benzotrifluoride—67–72%,
4-chloro-benzotrifluoride—2–5%,
2-chloro-benzotrifluoride—2.5–3%,
Various di-chloro-benzotrifluorides—18–24%.

The crude halogenation reaction mixture is then subjected to a nitration step under controlled temperature conditions which favor nitration of the mono halo isomers but at which the di-halo isomers do not undergo appreciable nitration. This not only has the advantage of lowering the number of potential off isomers produced in the nitration step, but as described hereinafter facilitates recovery of starting benzotrifluoride for recyle upon the reduction reaction of the last step. Applicants have also found that by avoiding appreciable nitration of the di-halo BTF isomers, a lower amount of MABT is produced.

The nitration step is effected by reacting the halogenated benzotrifluorides from the first step with nitric acid in the presence of sulfuric acid (or fuming $H_2SO_4$). This reaction may be schematically represented as follows:

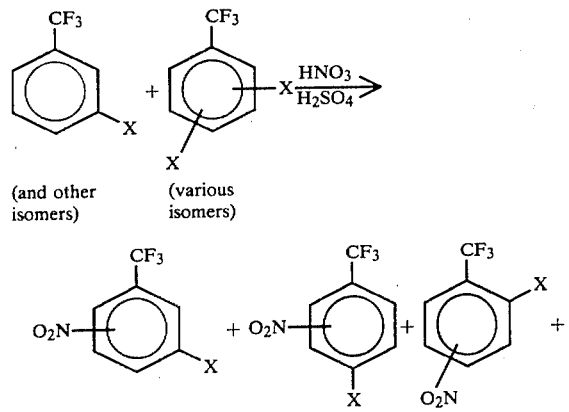

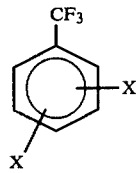

where X is Cl, or Br.

The presence of $H_2SO_4$ accelerates the rate of the nitration reaction and other materials known in the art to serve this function, such as $H_3PO_4$, may of course be used. Both $H_2SO_4$ and $HNO_3$ are preferably employed as substantially anhydrous materials (i.e., 98% solution). Nitric acid solutions containing about 70 to about 98% $HNO_3$ can also be used depending on the amount of $H_2SO_4$ employed. The reagents may be combined in any convenient manner in a suitable reaction vessel equipped with stirring and with provisions for cooling. In general, stoichiometric amounts of the crude substrate (i.e., total halogenated benzotrifluorides) and nitric acid can be employed although slight molar excesses of nitric acid may be employed and are generally preferred. The molar ratio of sulfuric acid to nitric acid is preferably in the range of from about 0:1 to 5:1, with about 2:1 being preferred.

In the preferred manner of operation, a mixture of nitric and sulfuric acids is added to the crude halogenated BTF mixture with vigorous stirring and with external cooling at a rate such that the reaction temperature does not rise above about 25° C. It is preferred to cool the crude reaction mixture to a temperature of less than about 5° C. prior to addition of the acid mixture. After completion of acid addition, the resulting two-phase mixture is stirred vigorously with the reaction temperature maintained in the range of from about 0° to 25° C. and preferably about 15° to 25° C. until no monohalobenzotrifluorides remain. Temperatures above about 25° C. begin to favor the nitration of di-halo isomers which are to be avoided according to the process of the present invention. The use of temperatures below about 25° C. also helps to avoid acid hydrolysis of the $CF_3$ group to a carboxylic acid group which undesirably can occur at higher reaction temperatures. Typically, reaction will be complete in from about 2 to 12 and preferably about 3 to 6 hours depending on the temperature and rate of stirring.

The major portion of the nitration products comprise various mononitro isomers of the monohalo-substituted benzotrifluorides produced in the first step reaction. As indicated above, the di-halo substituted benzotrifluorides do not nitrate to any appreciable degree under the reaction conditions specified for this nitration step. Typical yields of the nitration products are as follows:
2-nitro-5-chloro BTF—65–70%,
other nitro monochloro BTF isomers (3 major)—5–15%,
di-chloro BTF isomers (3 major)—16–22%,
nitro dichloro BTF isomers (5 major)—1–2%,
nitro BTF—1–4%.

After completion of the nitration reaction it is preferred to separate the organic phase from the acid phase. This can be accomplished, for example, by allowing layers to settle followed by decantation or the like. Phase separation may be facilitated by the addition of an organic solvent such as methylene chloride. In addition, it is preferable to extract the acid layer with an organic solvent such as methylene chloride to ensure all the products are recovered with the organic phase. Before subsequent processing, however, the methylene chloride or similar solvent should be removed, for example, by rotary evaporation or distillation. In a further embodiment, the recovered sulfuric acid may be used in subsequent nitration steps (i.e., recyled) after suitable dehydration.

The next step in the process according to the present invention is the catalytic reduction of the crude nitration mixture formed in the previous step in the presence of hydrogen, as schematically shown below:

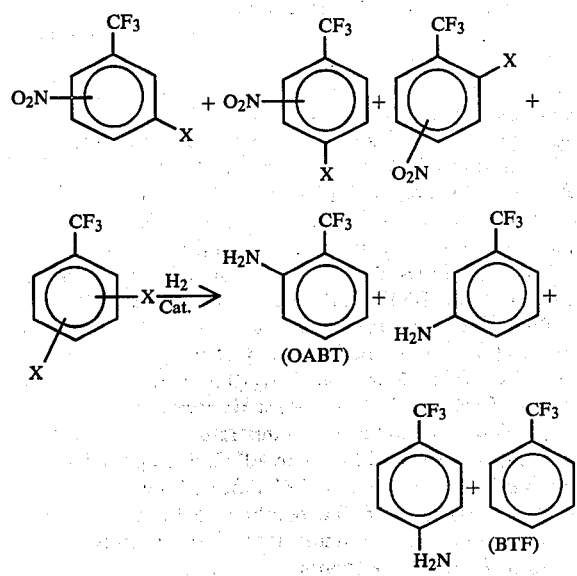

In this reaction, the various nitration products and the di-halo substituted BTF which did not nitrate are reacted with hydrogen in the presence of catalyst to reduce the nitro group to corresponding amine and to hydrodehalogenate the aromatic ring. While amounts of the $H_2$ uptake can be monitored to follow the reaction progress, typically about 3.6 mols of $H_2$ are supplied for each mol of crude nitrated mixture. The reaction should be effected in a suitable inert organic solvent. Among the wide variety of suitable solvents for this process are various polar solvents including alcohol, ethers, hydrocarbons, water and the like. Preferred are alcohols such as methanol or ethanol, optionally aqueous. In general, the concentration of the nitrated reactants in the solvent can range from about 20 to about 50% by weight.

The reaction mixture also includes an appropriate hydrogen halide scavenger, which can be selected from a wide variety of organic and inorganic bases. The scavenger neutralizes hydrogen halide as it is formed and solvent-soluble scavengers are preferred. Typical scavengers include ammonia (e.g., as a concentrated aqueous solution) triethylamine, trimethylamine, pyridine and di-isopropylethylamine. Triethylamine or ammonia are the preferred scavenger materials. The scavenger preferably is present in the reaction mixture at a level of at least about 1.2 mols per mol of crude nitrated mixture.

Preferred hydrogenation catalysts are metals such as palladium, platinum, rhodium, nickel and the like, which most often are available on porous supports. Most preferred are palladium on carbon catalysts which are commercially available in concentrations of 1 to 10% palladium. The supported catalysts are generally present in amounts less than 10% by weight of the reaction mixture.

The above-described reagents are preferably combined in a suitable pressure vessel equipped with means for stirring and introducing gaseous hydrogen. The hydrogenation reaction can be carried out at any suitable pressure from about 40 to 1000 psig. Preferred are reaction pressures of from about 100 to 200 psig.

The catalytic reaction takes place predominately in two stages, i.e., (1) hydrogenation of the nitro groups, and (2) hydrodehalogenation of the aromatic ring. The first reaction proceeds exothermally and external cooling of the reaction vessel, both initially and during the reaction, can be provided. It is preferred to cool the initial reaction mixture to about 15° to 20° C. Upon starting the flow of hydrogen to the vessel an extremely rapid exothermic reaction begins, during which it is preferred to keep the reaction temperature in the range of about 20° to 70° C. and preferably about 40° to 50° C. with suitable cooling. At this temperature, the primary reaction is the reduction of nitro groups to amine groups. When about three equivalents of hydrogen have been consumed, the exotherm ceases and the cooling can be stopped. The pressure vessel is then heated to an elevated temperature of from about 30° to 120° C. and preferably about 75° to 80° C. to facilitate the hydrodehalogenation reaction. Generally, the overall conversion process can be accomplished in about 1 to 24 hours, preferably about 3 to 5 hours.

The next step in the process of the present invention is the recovery of OABT and BTF from the crude reaction product. When the reduction reaction gas has gone to completion, i.e., no more hydrogen uptake is observed, the solution is cooled. Water is then added to dissolve ammonium chloride (if $NH_3$ is used as the scavenger) and the catalyst is filtered off. The filtrate can be treated with a saturated solution of sodium chloride to form two phases. The organic phase is then separated by decantation and the aqueous phase is washed with a suitable solvent such as methylene chloride. The combined organic phases can be dried, filtered and distilled to recover OABT product and BTF for use in recyle. For example, the crude reaction product can be distilled at about 15 mmHg through a ten tray Oldershaw column. At about 66° to 68° C. at 17 mm OABT distills off with less than about one percent of the contaminating meta- and para-isomers, even with straight take-over.

Yields of OABT recovered according to the process of the present invention typically are as high as 70-80%. Importantly the amount of MABT and para-aminobenzotrifluoride [PABT] isomers produced is considerably lower than previously achieved employing other processes. Typically the ratio of isomers in the product of this invention is approximately:

OABT—82%,
MABT—16%,
PABT—2%.

This represents significant improvement over the result obtained according to the process described in EPO Application No. 0 054 464 which purposely nitrates the di-halo BTF isomers formed in the halogenation step. That process is said to result in about 20-21% MABT and 77-78% OABT. This off-isomer (MABT) represents poor economics since it can be manufactured directly much more inexpensively. In contrast, the present process enjoys improved economics as a result of yields up to as high as 18% BTF which can be used for recycle to the first step of this overall process.

The following examples are included for illustrative purposes only and are not intended to limit the scope of the invention.

EXAMPLE 1

Chlorine (280 g, 4.0 mol) was bubbled slowly into a slowly stirred mixture of 301 g (2.06 mol) of benzotrifluoride, 0.91 g (0.014 g-atom) of iron powder and 0.85 g (0.0050 mol) of anhydrous $FeCl_3$ in a flask equipped with a dry ice—$CCl_4$ condenser to condense any starting material or product entrained in the HCl off gases. The reaction temperature slowly rose to 30° C. (from an initial temperature of 22° C.) and was maintained at 27°-30° C. by means of a cool water bath. The chlorination was stopped when 97% of the benzotrifluoride had been converted (10.5 hours total). Gas chromatographic analysis of the yellow mixture gave the following: 2.8% benzotrifluoride, 72.4% m-chloro BTF, 1.8% p-chloro BTF, 2.7% o-chloro BTF, 19.1% dichloro BTF (3 major isomers).

This mixture was nitrated directly in the same pot after cooling to 1° C. by addition of a mixture of 130.3 g (2.03 mol) of 98% $HNO_3$ and 396.9 g (4.05 mol) of 98% $H_2SO_4$ with vigorous stirring over the course of 20 minutes. The mixture warmed to 13° C. during the addition, then was stirred for 7.5 hours at 6°-10° C. to complete the nitration. The organic phase of the two phases mixture was separated and combined with a $CH_2Cl_2$ wash of the acid phase. This combined organic solution was washed with water and aqueous NaCl, then dried ($MgSO_4$). Evaporation gave 454.26 g of liquid having the following approximate analysis (by GC): 20% dichloro BTF (3 major isomers), 76% chloronitro BTF (4 major isomers).

Part of the crude nitration product (220.5 g, ~1 mol), was stirred in an autoclave with 73 g of 29% aqueous $NH_3$ (1.25 mol), 700 ml of methanol, 60 ml of $H_2O$ and 3.3 g of 5% Pd/C under an initial $H_2$ pressure of 800 psi. A rapid initial uptake of $H_2$ occurred and the exotherm was controlled with cooling, allowing a gradual rise in internal temperature. When the initial rapid reaction ceased (reaction temperature=50° C.), the autoclave was heated to 86° C. to complete the reduction. Hydrogen uptake was complete in 2 hr, 45 min at which time the mixture was cooled to 17° C., hydrogen was vented and 200 ml of $H_2O$ were added to dissolve precipitated $NH_4Cl$. The mixture was filtered to remove the catalyst and brine was added to separate the product mixture. The organic layer was drawn off and the aqueous phase was extracted with $CH_2Cl_2$. The combined organics were washed with $H_2O$, dried ($MgSO_4$) and distilled through a short Vigreux column. The aminobenzotrifluorides distilled at 52°-79° C. at 10 mm. Gas chromatographic analysis gave the following:

Yields from benzotrifluoride charged:
OABT—62.1%,
MABT—11.8%,
PABT—2.0%.

The foreruns contained benzotrifluoride corresponding to a 17.6% recovery.

EXAMPLE 2

A mixture of crude nitration product of Example 1 (216.3 g, about 1 mol), 120.6 g (1.19 mol) of triethylamine, 600 ml of methanol and 60 ml of $H_2O$ was stirred in an autoclave over 2.10 g of 10% Pd/C under an initial hydrogen pressure of 800 psi at 10° C. The initial exothermic reduction was controlled by a rapid flow of cooling water through the cooling coil of the autoclave. The exotherm ceased after 25 minutes at which time the internal temperature was 36° C. The mixture was then stirred for 4 hours while the internal temperature slowly fell to 26° C. After 4.5 hours total hydrogenation time, the catalyst was filtered off and water was added to separate the product. Gas chromatographic analysis indicated more than 96% conversion to benzotrifluoride and aminobenzotrifluorides.

EXAMPLE 3

Benzotrifluoride (730 g, 5 mol) was chlorinated at 25°-30° C. with 520 g (7.3 mol, 1.5 eq.) of chlorine and 4.0 g of 3:1 Fe:$FeCl_3$ catalyst over the course of 11 hours to 96% completion. The crude product (77% monochloro BTF's, 18% di-chloro BTF's by GC) was decanted from the catalyst and was nitrated by addition of a mixture of 329.5 g (5.13 mol) of 98% $HNO_3$ and 1027 g (10.5 mol) of $H_2SO_4$ with stirring at 5°-27° C. over 45 minutes followed by vigorous stirring for 4 hours at 15°-20° C. After normal workup, 1083.6 g of yellow liquid was obtained consisting of approximately 15% dichloro BTF's and 79% chloronitro BTF's.

Part of this mixture (53.64 g, about 0.25 mol) was reduced in 83 ml of methanol and 20 ml of $H_2O$ containing 17.4 g of 29% aqueous $NH_3$ (0.30 mol, 1.2 eq.) and 0.80 g of 5% Pd/C at a constant $H_2$ pressure of 100 psig in a 300 ml autoclave. The temperature of the reaction mixture was allowed to rise to 80° C. during the first 30 minutes and was held at 80° C. After 3 hours, 5 minutes GC analysis showed the reaction to be greater than 99% complete with aminobenzotrifluorides present in a ratio of 81.7:15.9:2.4 (o:m:p).

EXAMPLE 4

The following experiment is designed to show a direct comparison between the process of the present invention and that of EPO App. No. 0054464.

Benzotrifluoride (292.7 g, 2.0 mol) was chlorinated as above with 300 g of $Cl_2$ and 1.74 g of 3:1 Fe:$FeCl_3$ catalyst over the course of 8 hours to 98% completion. Gas chromatographic analysis gave the following after decantation from the solid catalyst: 1.78% BTF, 67.3% m-chloro BTF, 5.08% p-chloro BTF, 2.56% o-chloro BTF, 23.2% dichloro BTF (3 major isomers).

Low Temperature Nitration

Half of the crude chlorinated mixture (184.0 g, about 1 mol) was nitrated by addition of a mixture of 65.12 g (1.03 mol) of $HNO_3$ and 198.4 g (2.02 mol) of $H_2SO_4$ at 1°-16° C. over 20 minutes followed by vigorous stirring at 8-18° C. for 5 hours, 20 minutes. Normal workup gave 215.9% of yellow liquid having the following analysis: 18% dichloro BTF (3 major isomers), 77% chloronitro BTF (4 major isomers), 2.3% dichloronitro BTF (5 major isomers).

Part of this crude nitration product (37.77 g, about 0.175 mol) was reduced in a mixture of 105 ml of methanol and 10.5 ml of water containing 12.9 g (0.220 mol) of 29% aqueous $NH_3$ and 0.56 g of 5% Pd/C at 540 psig of $H_2$ pressure in a 300 ml autoclave. After the initial exotherm (controlled with cooling to maintain the temperature below 60° C.) the mixture was held at 80° C. for 2 hours, 10 minutes (total reduction time=3 hours, 10 minutes). After normal workup, gas chromatographic analysis indicated the reduction to be greater than 99.5% complete with aminobenzotrifluorides present as follows:
OABT—81.2%,
MABT—15.4%,
PABT—3.4%.

High Temperature Nitration

The remaining half of the crude chlorinated BTF mixture from above (183.9 g, about 1 mol) was nitrated by addition of a mixture of 100.9 g (1.60 mol) of $HNO_3$ and 157.2 g (1.60 mol) of $H_2SO_4$ at 10° C. over 56 minutes followed by vigorous stirring for 11 hours at 80° C. Normal workup gave 223.7 g of yellow liquid with the following analysis: 0.4% dichloro BTF, 1.6% nitro BTF, 75% chloronitro BTF (4 major isomers), 22% dichloronitro BTF (5 major isomers).

Part of this mixture (39.16 g, about 0.175 mol) was reduced in 105 ml of methanol and 10.5 ml of water containing 12.9 g (0.220 mol) of 29% aqueous $NH_3$ and 0.57 g of 5% Pd/C at 520—550 psig of $H_2$ pressure in a 300 ml autoclave. After the initial exotherm (controlled with cooling), the mixture was maintained at 80° C. for 4 hours followed by a further 5.5 hour reduction period at 80° C. and 550 psig (analysis after 4 hours indicated incomplete reduction). After normal workup, gas chromatographic analysis indicated the reduction was greater than 99.5% complete with aminobenzotrifluorides present as follows:
OABT—70.9%,
MABT—25.1%,
PABT—4.0%.

Since modifications will be apparent to those skilled in the art, it is intended that the invention be limited only by the scope of the appended claims.

We claim:
1. A process for preparing ortho-aminobenzotrifluoride which process comprises the steps of:
 (a) reacting benzotrifluoride with a halogen selected from the group consisting of chlorine and bromine in the presence of a halogenation catalyst selected from the group consisting of $FeCl_3$, $Fe/FeCl_3$, and $SbCl_5$ to produce a crude halogenation reaction mixture containing meta-halobenzotrifluoride and other mono and di-halo substituted benzotrifluorides;
 (b) reacting said crude halogenation reaction mixture with nitric acid in the presence of sulfuric acid to form a crude organic nitration reaction mixture, said reaction being carried out at a temperature at which the monohalobenzotrifluoride isomers are preferentially nitrated but the di-halo isomers do not undergo appreciable nitration;
 (c) reacting said organic nitration reaction mixture with hydrogen in the presence of a hydrogenation catalyst and a hydrogen halide scavenger to produce a mixture of ortho-aminobenzotrifluoride, other amino-substituted isomers of benzotrifluoride and unsubstituted benzotrifluoride; and
 (d) separately recovering ortho-aminobenzotrifluoride product and recyclable benzotrifluoride for use in step (a).

2. The process of claim 1 wherein said halogen is chlorine and said halogenation catalyst is $Fe/FeCl_3$.

3. The process of claim 1 wherein the nitration reaction of step (b) is carried out at a temperature of from about 0° to about 25° C.

4. The process of claim 1 wherein said hydrogenation catalyst is palladium supported on charcoal.

* * * * *

UNITED STATES PATENT AND TRADEMARK OFFICE
CERTIFICATE OF CORRECTION

PATENT NO.   :   4,469,890
DATED        :   September 4, 1984
INVENTOR(S)  :   John P. Chupp, Thomas E. Neumann, Michael J. Miller It is certified that error appears in the above-identified patent and that said Letters Patent is hereby corrected as shown below:

Column 7, line 30:   "phases" should be --phase--

Column 8, line 55:   "215.9%" should be --215.9 g--

Signed and Sealed this

Twelfth Day of February 1985

[SEAL]

Attest:

DONALD J. QUIGG

Attesting Officer        Acting Commissioner of Patents and Trademarks